United States Patent [19]

May, Jr. et al.

[11] 4,419,999

[45] Dec. 13, 1983

[54] METHOD AND APPARATUS FOR MONITORING VASCULAR FLOW

[76] Inventors: James W. May, Jr., Sandy Pond Rd., Lincoln, Mass. 01773; Frederick N. Lukash, 444 Lakeville Rd., Lake Success, N.Y. 11042; Kenneth H. Cohn, 94 Francis St., Brookline, Mass. 02146

[21] Appl. No.: 327,785

[22] Filed: Dec. 7, 1981

Related U.S. Application Data

[63] Continuation-in-part of Ser. No. 255,247, Apr. 17, 1981, abandoned.

[51] Int. Cl.$^3$ .............................................. A61B 5/02
[52] U.S. Cl. .................................... 128/691; 128/736; 73/204
[58] Field of Search .................... 128/691, 736, 663; 73/204

[56] References Cited

U.S. PATENT DOCUMENTS

| | | | |
|---|---|---|---|
| 3,568,661 | 3/1971 | Franklin | 128/663 |
| 3,589,360 | 6/1971 | Sinclair | 128/2.05 F |
| 3,623,473 | 11/1971 | Anderson et al. | 128/691 |
| 3,651,694 | 6/1972 | Lamb | 128/736 |
| 4,191,194 | 3/1980 | Watanabe et al. | 128/692 |

FOREIGN PATENT DOCUMENTS

| | | | |
|---|---|---|---|
| 1121274 | 4/1956 | Fed. Rep. of Germany | 128/691 |
| 2843133 | 3/1980 | Fed. Rep. of Germany | 128/691 |
| 2393283 | 12/1978 | France | |
| 2411392 | 8/1979 | France | 128/691 |

OTHER PUBLICATIONS

Morris, R; Polak, E; and Serafin, D., "Assessment of Viability in Transplanted Tissue-Electromagnetic Flowmeter." *Microsurgical Composite Tissue Transplantation*, Serafin, D. and Bunke, H. J., Editors, C. V. Mosby Company, 1979.
Baker, D. W. and Holloway, G. A., Jr. "Assessment of Viability in Transplanted Tissue-Doppler Techniques Using Acoustic (Ultrasound) and Optical (Laser) Techniques." *Microsurgical Composite Tissue Transplantation*, Serafin D. and Buncke, H. J., Editors, C. V. Mosby.
Stirrat, C. R.; Seaber, A. V.; Urbaniak, J. R.; and Bright, D. S. Temperature Monitoring in Digital Replantation, *J. Hand Surg* 3:343, 1978.
In Guyton, A. C., Editor, *Textbook of Medical Physiology*, 1976, 5th Edition, W. B. Saunders Company, p. 950.
Priebe, Conf: Int. Symon Biotelem., Netherlands, May 5–8, 1981, pp. 65–72.
Challoner, Med. & Bio. Eng. vol. 13, No. 2, pp. 196–201, Mar. 1975.
Larsson, et al., Med. & Bio. Eng. & Comp. Mar. 1980.
Weiland, et al., "Free Vascularized Bone Grafts in Surgery of the Upper Extremity".
Reinisch, J. F., "The Pathophysiology of Skin Flap Circulation" The Delay Phenomenon.
May, et al., "The No-Reflow Phenomenon in Experimental Free Flaps".
Jobsis, et al., "Optical Monitoring as a Research and Clinical Method to Assess Tissue Metabolism and Blood Flow", *Microsurgical Composite Tissue Transplantation*, Serafin, D. and Bunke, H. J., Editors, C. V. Mosby Company, 1979.
Woodcock, J. P. "Physical Properties of Blood and Their Influence on Blood-Flow Measurement", *Reports on Progress in Physics*, 1976, vol. 39, No. 1, pp. 65–127.
Colette et al., *International Conference on Biomedical Transducers*; Paris, 3–7 Nov. 1975, Coll. 1975; pp. 469–471.
Ellenwood, et al., "Implantable Temperature Probe having Pull Tab", *IBM Technical Disclosure Bulletin*, vol. 17, No. 1, Jun. 1974.

*Primary Examiner*—Kyle L. Howell
*Assistant Examiner*—J. C. Hanley
*Attorney, Agent, or Firm*—Lahive & Cockfield

[57] ABSTRACT

A method and device for measuring blood flow through a blood vessel within human or animal bodies. It utilizes the principle of energy conversion to heat by myocardial activity, organ metabolism, and laminar frictional flow in blood vessels and measures the heat dissipation through the vessel wall with obstruction to flow. When the device of the invention is placed next to the vessel wall, the output signal correlates blood flow with temperature. With an obstruction to flow, the temperature drops. The device is placed in series proximal and distal to the repaired vessel to be studied. The leads are brought through the skin and attached to a temperature monitor.

5 Claims, 8 Drawing Figures

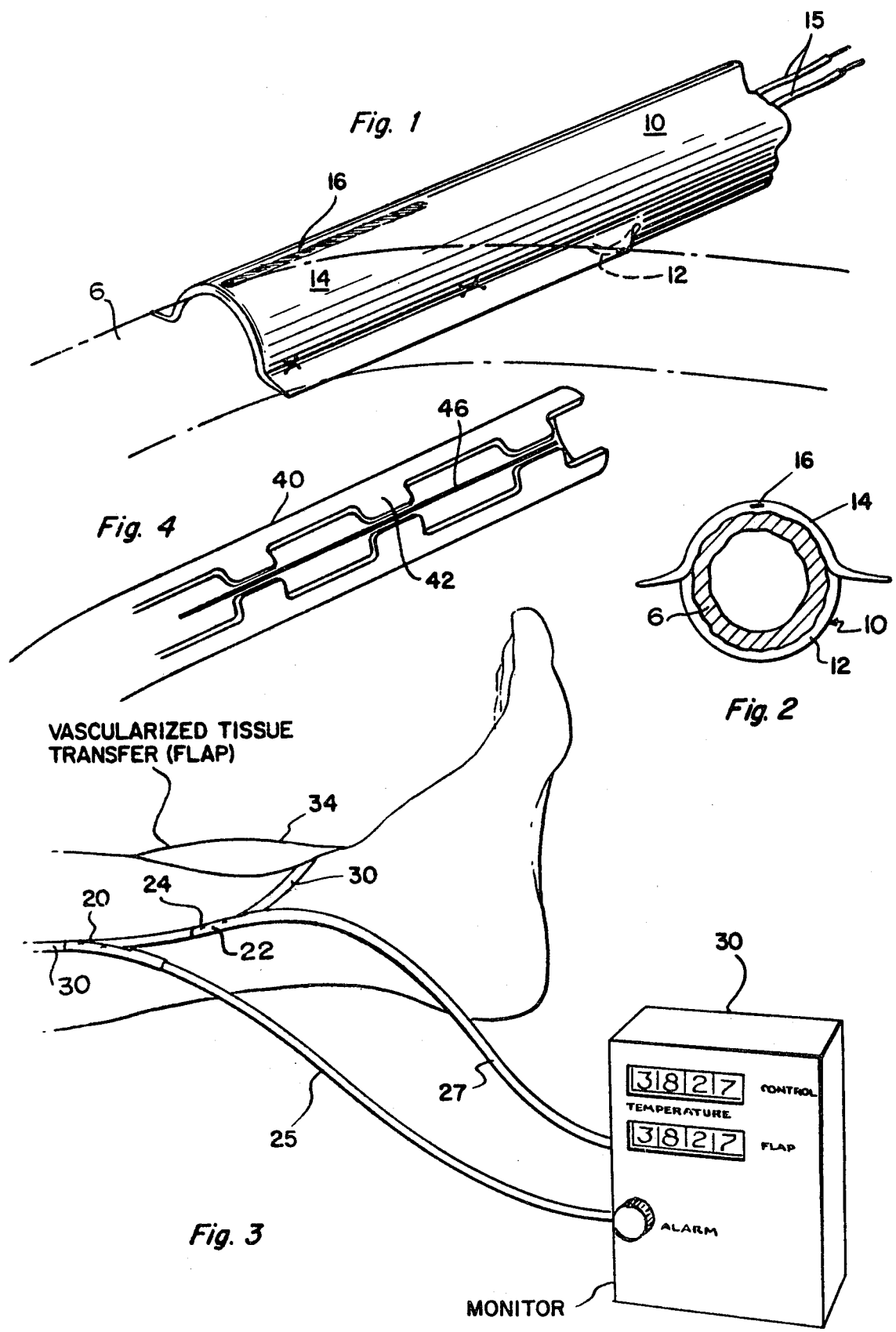

CFA – COMMON FEMORAL ARTERY
SFA – SUPERFICIAL FEMORAL ARTERY
PFA – PROFUNA FEMORIS ARTERY
IEA – INFERIOR EPIGASTRIC ARTERY
▬ MONITOR

METHOD AND APPARATUS FOR MONITORING VASCULAR FLOW

CROSS REFERENCE TO RELATED APPLICATIONS

This application is a continuation-in-part of the co-pending application Ser. No. 255,247 entitled "Method and Apparatus For Monitoring Vascular Flow" and filed on Apr. 17, 1981 now abandoned.

BACKGROUND OF THE INVENTION

This invention relates in general to a method and apparatus for measurement of blood flow and more particularly to the measurement of blood flow with an implantable device, especially suitable for use in conjunction with both micro- and macrosurgical procedures.

The principle of reconstructive vascular surgery is to provide and maintain blood flow to tissues and organs. With circulatory interruption distal tissues become ischemic. Over time this ischemia progresses from a reversible form (one in which restoration of blood flow re-establishes tissue viability) to an irreversible form (one in which there is cell death and irrevocable tissue damage).

Of prime importance is the monitoring of the patients, specifically the area which has been vascularized, so that if there is circulatory embarrassment it is discovered during the period of reversible ischemia. With early intervention and correction, tissue viability is restored and preserved.

Various techniques have been employed in the past for measuring blood flow in large and small blood vessels. These have included direct observation (blanche and refill technique) in tissues with a cutaneous component; Doppler and ultra sound monitors; transcutaneous oxygen probes; laser optic monitors; tracer scans; arteriography; and electromagnetic flow meters. All of these methods are limited in that they are either episodic in their monitoring, risky in their application, or not entirely reliable in their interpretation.

What is needed is a monitor that can be placed under direct vision next to a vessel and which would give continuous, reliable information regarding blood flow through that vessel; and one which would warn of any flow abnormalities. When no longer needed, the monitor should have the ability to be removed atraumatically and transcutaneously. Its use should be valid in all types of vascular surgery (microsurgical, macrosurgical) and in all types of repairs (arteries, veins, vein grafts, prosthetic grafts). Uses may also include monitoring organ function, for example for diagnosis.

SUMMARY OF THE INVENTION

Broadly speaking, the present invention in one aspect measures blood flow within vessels by measuring the temperatures of the blood vessels, both proximal and distal to an anastomatic repair. This may be done by measuring these temperatures that exist ambiently within the body on a continual basis or by providing heat to the system and noting the rates of dissipation proximal and distal to the anastomatic repair. The device of the invention includes a thermal sensor which can be placed over a portion of the blood vessel with leads taken out transcutaneously to a temperature monitor.

DESCRIPTION OF THE DRAWING

In the drawing:

FIG. 1 is an illustration in perspective view of a blood flow sensor constructed in accordance with principles of this invention;

FIG. 2 is a cross-sectional view of the sensor of FIG. 1;

FIG. 3 is an illustration of sensors constructed in accordance with principles of this invention attached at proximal and distal locations on a blood vessel for practicing the method of the invention;

FIG. 4 is an illustration in perspective view of a different embodiment of a sensor constructed in accordance with principles of this invention.

DESCRIPTION OF PREFERRED EMBODIMENTS

Figure 5A:
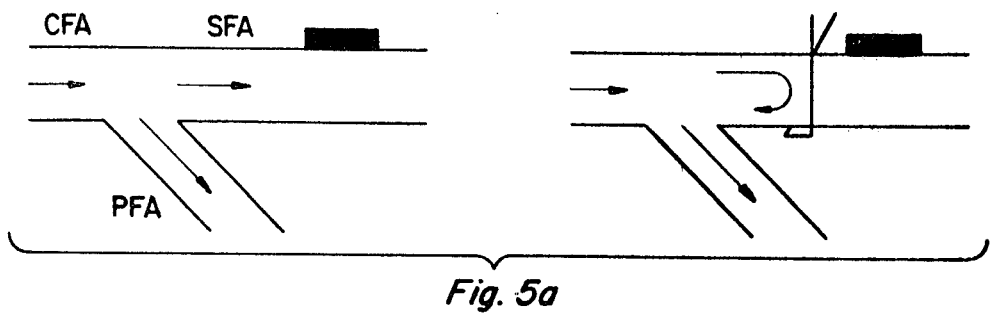
FIGS. 5a, b, c and d are illustrations in generally schematic form of an example of the practice of the method of this invention.

Referring to FIGS. 1 and 2, there is illustrated one embodiment of the device of the invention. A silicon elastomer tubing 10, which typically would be formed of a tubing having 1.1 mm internal diameter and 1.7 mm external diameter, has one end cut away leaving a semi-lunar cap section 14, in which is embedded a thermal sensor in the form of a thermocouple 16. Electrical leads 15 from the thermocouple 16 are brought out through the full tubing section 12 of the elastomer tube. The semi-lunar cap, or sheath, is placed in close juxtaposition around blood vessel 6, with the thermocouple element 16 immediately adjacent to the adventitia of the vessel. The thermocouple 16 may be any suitable thermocouple such as those manufactured as type T by Omega Electronics, Hartford, Conn. A suitable thermocouple was made by stripping Teflon insulation from the ends of matched, 3 mil constantan and chromel alloys. After twisting the ends together on one side and soldering them, the thermocouple junction was insulated by dipping in a dilute solution of lacquer and glyptol. While a thermocouple is illustrated in FIG. 1, the temperature sensor could be formed of a thermistor or any other suitably sized, suitably sensitive, temperature detector.

The polymer housed thermocouple unit which FIGS. 1 and 2 illustrate is specifically designed such that the thermocouple and its insulation are enclosed within the polymer cylinder. The polymer cylinder is flattened and semilunar at one end and is structured in such a way to allow the thermocouple junction to remain only a fraction of a millimeter from the surface temperature to be measured. The polymer housing is constructed in such a way as to allow laxity of thermocouple wiring within the polymer housing such that any longitudinal traction on the housing will not disrupt and damage the thermocouple. Further, the polymer housing of a silicone or other typical innert flexible, stretchable and malleable material is made in such a way as to allow a suture needle to be driven easily through the housing with which attachment of the housing to an appropriate tissue location can be utilized. The various sizes of the polymer housing are made to appropriately fit the tissue mounting purpose which is required in the specific clinical use. Further, the housing is constructed in such a way with a smooth external surface such that adherence to surrounding tissues is minimized and, thus, the entire unit can be extracted transcutaneously from the indwelling wound in a trauma-free way.

With reference to FIG. 3, the blood flow detector of the invention is shown implanted within the human leg. In this embodiment, a control sensor 20 is sutured to the perivascular tissue around artery 30 at a location above the point of anastomisis to the artery of the vascularized tissue transfer (flap) 34. A second probe 22, identical to the first, is sutured, again through sutures 24 to the perivascular tissue around the artery 30 at a point proximal to the vascularized tissue flap 34. The leads 25 and 27, respectively, from the control probe and the flap probe, are brought out through the skin to connect to a temperature monitor 30. The monitor as is illustrated schematically can present separate readings for temperature of the control probe and the flap probe, or could be arranged to provide only a differential temperature output. Additionally, the monitor 30 is shown as providing an alarm, which will provide a visual or audio output when the differential between the temperature at the control probe and the flap probe exceeds a predetermined amount. A suitable monitor is that sold under the type designation TH-6, by Bailey Instrument Inc. of Saddle Brook, N.J.

Procedurally, the probes illustrated in FIGS. 1, 2 and 3, are attached with sutures to the tissue around the artery after completion of the surgical anastomisis, and the leads are taken out through the skin in a manner similar to drains. The wound is then closed and the temperature monitored on a continual basis. It has been found, in animal tests, that occlusion of the artery will result in a temperature drop of approximately 1° Centigrade. This is in contrast to a significantly lesser drop in temperature as measured by the two probes when the artery is patent. When the monitor is no longer needed, approximately 72 hours after completion of the surgery, the sutures 24 have absorbed and the leads may be atraumatically and transcutaneously removed.

In FIG. 4 there is illustrated a second embodiment of a sensor configuration suitable for use in the invention. In the probe of FIG. 4, the silicon elastomer tubing 40 has had a section at the end cut as shown to produce a series of tabs 42. A heat sensor 46, which would typically be a thermistor or thermocouple, is again embedded in the upper wall of the sheath in a manner similar to that described for the embodiment of FIG. 2. In application, the probe of FIG. 4 is slipped over the artery and is held in place by virtue of the gripping action of the tabs 42. In this embodiment, then, no sutures would be utilized.

A sensor or probe for practice of the invention thus has a support element that carries a thermal sensor element. The support element is of readily sterilized, surgical grade, electrically insulating material which is chemically inert to the body in which it is implanted. Further, to facilitate removal of the probe, the material is of a character to which body tissue does not adhere or cling and into which tissue does not grow. The support element is configured to dispose the thermal element in the desired heat transfer relation with the tissue being monitored. The illustrated support element structures have at least a partial tubular configuration to dispose the thermal element close to, if not contiguous with, a vascular body member, e.g. a vessel. In one illustrated instance, i.e. FIG. 1, the support element is sutured in place, and in another instance, i.e. FIG. 4, the support element is configured for resiliently and releasably attaching to the vascular member.

The support element preferably is arranged, moreover, for atraumatic and transcutaneous removal from the implantation site being monitored simply upon pulling on the electrical leads from the thermal element. This feature of a support element according to the invention calls for the probe to be elongated longitudinal with the extension of the leads from the sensor element and to have sufficient pliability and streamlined configuration (e.g. be free of rigid lateral protruberances) for safe extraction in this manner from the body in which it is implanted.

As further described, the thermal sensor element of the probe is affixed to the support element, typically on or recessed in an inner tubular surface thereof.

Figure 5B:
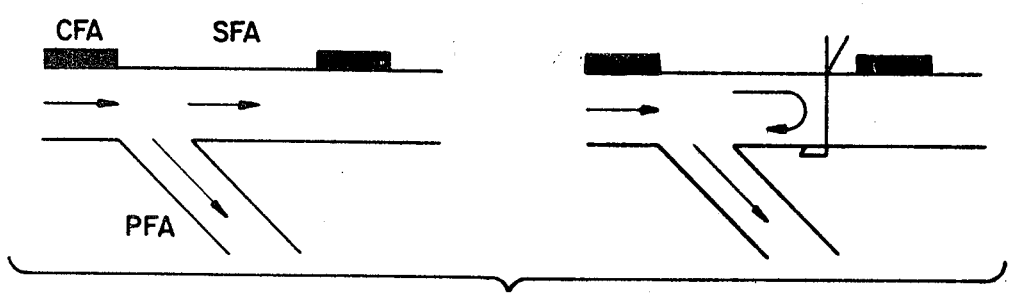
Figure 5C:
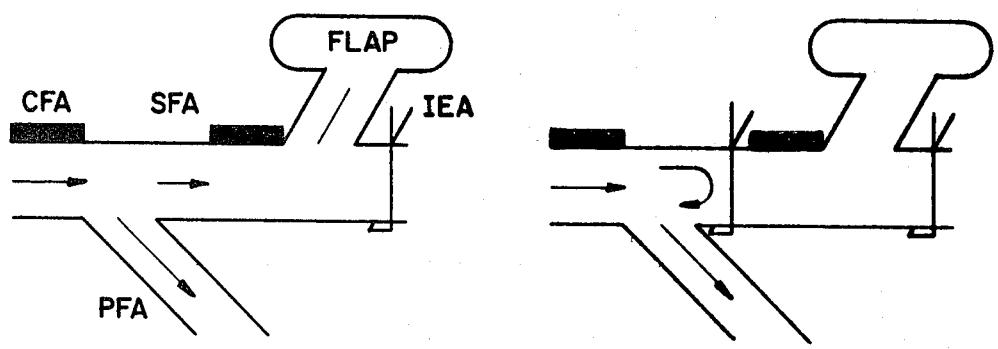

In FIG. 5 there is illustrated a series of experiments demonstrating the method of this invention, utilizing the principles of heat generation through frictional flow. Thermistor monitors were used to correlate temperature drops with occlusions in one-to-two mm blood vessels in experimental animals. In Sprague-Dawley rats, New Zealand white rabbits, and mongrel dogs, three flow-occlusion models were tested with implantable thermistor monitors to directly measure vessel temperature. In FIG. 5a there is illustrated a single sensor monitoring of a femoral artery with repeated occlusions and releases. This experiment was carried out with six 300 mg Sprague-Dawley rats. In FIG. 5b, there is illustrated schematically the simultaneous monitoring of a femoral artery with monitors proximal and distal to a situs of occlusion. This experiment was carried out with three 300 mg Sprague-Dawley rats, two 3 kg New Zealand white rabbits and two 30 kg mongrel dogs. In FIG. 5c there is illustrated the simultaneously monitoring of the arterial inflow into an isolated epigastric flap, based on the inferior epigastric vessels, with and without occlusion. This experiment was carried out on five 3 kg New Zealand white rabbit.

In all of the experiments illustrated schematically in FIG. 5 the blood vessels were exposed and the sensors secured with the thermistors flush to the adventitia of the particular vessels. The signal lines from the sensors were brought out through separate sites. A standard vessel occlusion loop was placed around the femoral artery and also brought out with a small catheter through a separate opening. The wounds were then closed. Free flowing base line data was established and thereafter the vessels were occluded. After data related to the occlusion was recorded, the occlusion loop was reopened and flow data again recorded. At the conclusion of each of the experiments the sensors were removed transcutaneously and the wound was then opened and the vessels examined for injury.

The results of the above described experiments were as follows:

(a) the occlusion of the vessels in the rats resulted in a 1° Centrigrade drop in temperature at the point distal to the point of occlusion, (b) occluding the blood vessels in rabbits and dogs resulted in a 0.5° Centigrade drop in temperature at a point distal to the point of occlusion, (c) in all of the experiments reestablishment of the flow following the removal of the occlusion resulted in a all of the temperature readings returning to the previous base line, (d) the transcutaneous removal of the sensor resulted in no trauma to the blood vessels.

In the preferred method described the blood flow through the vessels results in maintenance of temperature at the sensors, while occlusion results in decreased temperature. However, there may be situations, for example in locations deep within a body, where the ambient temperature is sufficiently high so that even when the vessel is occluded the temperature will not drop appreciably. One method which may be used under such circumstances is to provide heat to the sensors, for example electrical current to the thermocouples. Blood flow through the vessel will then cool the thermocouples at an essentially equal rate. If, however, there is an occlusion, the lack of flow within the vessel at the sensor distal to the occlusion will result in a slower rate of cooling at that sensor. This differential may be monitored by conventional techniques, thus providing an indication of occlusion.

It is believed that the utility of the heat sensing probe techniques and devices of this invention in diagnosing vascular disturbance within a free tissue transfer can include topical application of the probe on the surface of the free tissue transfer or within the substance of the transfer itself. Although the temperature differential between a proximal vessel and a distal vessel supplying the transfer, as exemplified in the foregoing illustrated embodiments, may be amongst the most sensitive methods of tissue transfer monitoring, it is considered that other sources of heat production may be used as the control source within the body, such as an adjacent viscus or muscle which is deep within the body or extremity, and utilize the parenchyma of the transferred tissue as the monitoring surface analogous to the distal artery. This technique may be particularly useful where the medical risk of placing the probe in contact with the vessel is extensive and there is acceptable reliability in placing the thermocouple in contact with the tissue to be transferred or a proximal heat source.

Having described the invention, various modifications and additions will occur to those skilled in the art, and the invention should be construed as limited only by the spirit and scope of the appended claims.

We claim:

1. In the measurement of blood flow at a selected site in tissue of an animal body by monitoring temperature with sensor means, the improvement comprising the steps of
   A. providing electrical thermal sensor means having electrical leads extending therefrom,
   B. providing an implantable housing element configured to conform with a portion of a blood vessel and carrying said sensor means on a surface thereof for disposition contiguous with a vessel adjacent to which said element is implanted,
   C. surgically implanting said housing element within the animal body next to the wall of a vessel in which said blood flow is to be measured, for implanting said sensor means contiguous with tissue of the body and with said electrical leads extending transcutaneously therefrom,
   D. monitoring temperature sensed by said implanted housing-carried sensor means by monitoring the electrical signal on said leads, for providing an indication of relative blood flow in said vessel, and
   E. adapting said housing element with said sensor means for atraumatic removal from said body by transcutaneous withdrawal from said surgically-implanted location by pulling on said electrical leads.

2. In the measurement of blood flow according to claim 1, the further improvement
   A. wherein said surgically-implanting step includes implanting a first thermal sensor at a distal position relative to the selected site, and
   B. including the step of placing a second thermal sensor of the animal body temperature at a proximal position relative to said site.

3. In the measurement of blood flow according to claim 1, the further improvement wherein said surgically-implanting step includes implanting said housing element for disposing said thermal sensor means for sensing temperatures at the adventitia of the blood vessel in which said blood flow is to be measured.

4. In apparatus for the measurement of blood flow in tissue of an animal body by monitoring tissue temperature, a surgically-implantable temperature-sensing device comprising
   A. a surgically-implantable temperature sensing element having electrical signal conductors, said temperature sensing element providing on said conductors an electrical output signal indicative of its temperature, and
   B. a surgically-implantable housing element of biologically inert suturable material, said housing element having a semi-lunar portion with a tubular configuration conforming to a blood vessel and having said sensing element fixed at a tubular inner surface thereof for disposition contiguous with tissue in which said housing element is implanted, said housing element with said sensing element fixed thereto having an elongated configuration adapted for atraumatic and transcutaneous removal from surgical implantation upon the application of tension to said signal conductors.

5. In apparatus according to claim 4, the improvement wherein said sensing element includes a thermocouple sensor.

* * * * *